United States Patent [19]

Hart

[11] Patent Number: 4,494,543
[45] Date of Patent: Jan. 22, 1985

[54] INSTRUMENT FOR EXTRACTING SPLINTERS

[76] Inventor: Ernest D. Hart, 4006 E. Andrews, Fresno, Calif. 93726

[21] Appl. No.: 354,144

[22] Filed: Mar. 5, 1982

[51] Int. Cl.³ .............................................. A61B 17/30
[52] U.S. Cl. .................................................... 128/354
[58] Field of Search ................... 128/354, 314, 329 R, 128/330, 329 A, 355, 303.13, 303.18; 81/43

[56] References Cited

U.S. PATENT DOCUMENTS

| | | |
|---|---|---|
| 853,096 | 5/1907 | Lewis . |
| 1,433,340 | 10/1922 | Clark . |
| 1,677,170 | 4/1928 | Segal . |
| 2,894,512 | 7/1959 | Tapper ............................ 128/303.18 |
| 2,934,070 | 4/1960 | Jerry . |
| 3,054,405 | 9/1962 | Tapper ............................ 128/303.18 |
| 3,971,386 | 7/1976 | Yamada . |
| 4,171,701 | 10/1979 | Walter et al. ......................... 128/354 |
| 4,240,435 | 12/1980 | Yazawa et al. ...................... 128/354 |
| 4,375,815 | 3/1983 | Burns ................................ 128/329 R |
| 4,388,925 | 6/1983 | Burns ................................ 128/329 R |

Primary Examiner—C. Fred Rosenbaum
Assistant Examiner—Michelle N. Lester
Attorney, Agent, or Firm—Huebner & Worrel

[57] ABSTRACT

An instrument for extracting splinters and the like, having a hollow elongated handle; a pair of resilient arms, the arms being mounted externally on the handle, having jaws disposed outwardly of a tip end of the handle, and extending along the handle toward its opposite end; a rod having a piercing end at the tip end of the handle and being slidably received within the cavity for movement between an operating position in which the piercing end extends outwardly of the jaws and a sheathed position in which this end is adjacent to the tip end; a spring urging the rod toward the sheathed position; a plunger extending within the cavity at such opposite end to engage the rod and having a button to press the rod into the operating position; a latch mounted on the plunger for latching the rod in this position; and a trigger operable by pressing one of the arms toward the handle to unlatch the rod from the handle for return by the spring to the sheathed position.

5 Claims, 3 Drawing Figures

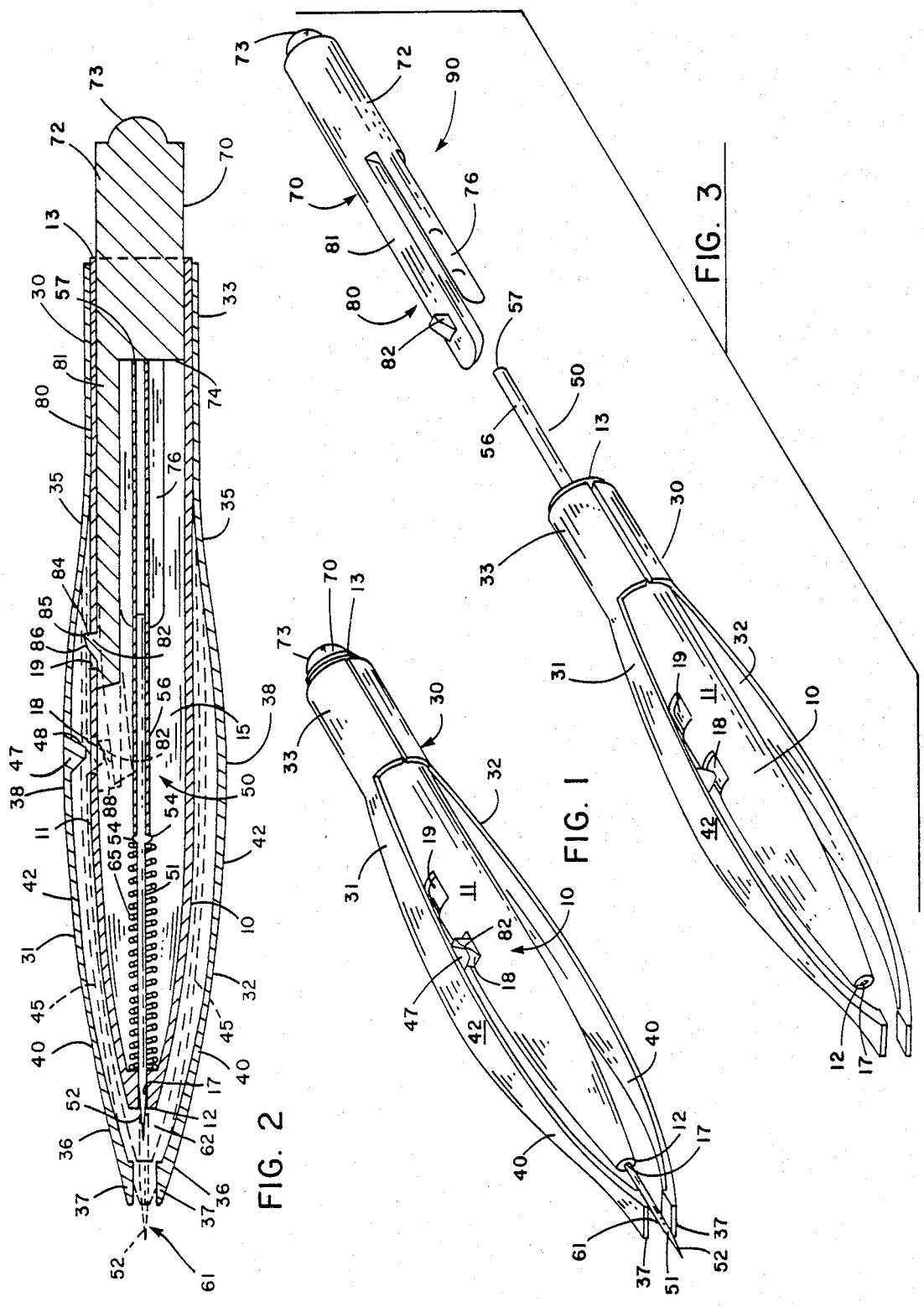

INSTRUMENT FOR EXTRACTING SPLINTERS

BACKGROUND OF THE INVENTION

1. Field of the Invention

The present invention relates to an instrument for extracting splinters, and more particularly to such an instrument for obtaining access to thorns, splinters, and the like objects embedded in flesh and for grasping such an object to remove it.

2. Description of the Prior Art

The prior art includes a variety of instruments having a piercing element mounted on a grasping device for convenience in removing splinters and the like, access to an embedded splinter being obtained with the piercing element and the exposed splinter being grasped and extracted with the device. It is also known to mount the piercing element on the device for selective retraction or extension so that the device serves as a sheath for the element. However, insofar as known to the applicant, such prior art instruments, although effective for piercing, grasping and sheathing, the piercing element has certain deficiencies. For example, many such prior art instruments require reversal of the instrument in the hand after use of the piercing element to shift to its use of the grasping device. Another deficiency of certain such prior art instruments is that they do not provide for positive latching of the piercing element in its retracted position and/or its extended position. As a result, the piercing element inadvertently retracts while being used or extends when it should be sheathed. Another such deficiency is that manipulation of the instrument to retract the piercing element is relatively inconvenient, causing a delay at the moment the splinter is exposed for extracting. A deficiency of certain such prior art instruments is that the piercing element is not conveniently removable for replacement and cleaning.

PRIOR ART STATEMENT

The following patents, copies of which are enclosed together with Form PTO-1449, are submitted in conformance with 37 C.F.R. §1.97 and §1.98 and characterize the closest prior art of which the applicant is aware:

| Lewis | 853,096 | May 7, 1907 |
| Clark | 1,433,340 | Oct. 24, 1922 |
| Segal | 1,667,170 | Apr. 24, 1928 |
| Jerry | 2,934,070 | Apr. 26, 1960 |
| Yamada | 3,971,386 | July 27, 1976 |

The Lewis U.S. Pat. No. 853,096 is believed relevant in its disclosure of an instrument having a needle disposed centrally between the jaws of a forceps. The needle is removable but is not selectively extendable or retractable.

The U.S. Pat. No. 1,433,340, to Clark, and U.S. Pat. No. 3,971,386, to Yamada, are believed relevant in their disclosure of instruments having a needle which is selectively retractable into the closed end of a pair of tweezers. The instrument thus requires reversal after use of the needle in order to grasp a splinter.

U.S. Pat. No. 1,667,170 to Segal discloses an instrument which has arms which, when squeezed together, close a pair of jaws and draw the closed jaws over a wiper centrally therebetween.

The U.S. Pat. No. 2,934,070 to Jerry is believed relevant in its disclosure of an instrument having a needle selectively retractable within and extendable from between the jaws of a pair of tweezers.

The prior art also includes certain elements of the subject invention which are subsequently to be described and are utilized to disassemble the instrument and to retract or extend a piercing element thereof.

SUMMARY OF THE INVENTION

It is an object of the present invention to provide an improved instrument for extracting splinters and the like.

Another object is to provide such an instrument which is highly convenient to use in that the grip does not have to be substantially altered to change the instrument from a piercing configuration, for exposure of a splinter, to a grasping configuration, to seize and remove the splinter, and in that only the simplest manipulation is required to place the instrument in its piercing configuration.

Another object is to provide such an instrument in which the piercing element is easily removable for replacement and cleaning.

Another object is to provide such an instrument having the foregoing advantages in which the piercing element is securely held in an operating position and in a sheathed position.

A further object is to provide improved elements and arrangements thereof in an instrument for extracting splinters and the like which has the above and other objects and advantages and is economical, durable and fully effective in carrying out its intended purposes.

BRIEF DESCRIPTION OF THE DRAWINGS

FIG. 1 is a perspective view of an instrument for extracting splinters and the like; the instrument embodies the principles of the subject invention and is depicted in a piercing configuration.

FIG. 2 is a transverse section of the instrument of FIG. 1 at an enlarged scale and in a grasping configuration, the position of certain elements in the piercing configuration being depicted in dash lines.

FIG. 3 is a perspective view of the instrument of the same scale as FIG. 1 in a partially disassembled configuration.

DESCRIPTION OF THE PREFERRED EMBODIMENT

Referring with greater particularity to the drawings, the figures depict an instrument which embodies the principles of the subject invention and is for extracting splinters, thorns, and the like from the flesh of the fingers or other parts of the body.

The instrument has a handle 10 which is of generally cylindrically tubular shape and has a side wall bearing an exterior surface 11. The handle is elongated along its axis and has a tip end 12 and a longitudinally opposite base end 13. The handle defines a cavity 15 extending through it axially and opening through each of the opposite ends. The cavity opens through the tip end by way of a cylindrical bore 17. Exteriorly and toward the tip end, the handle 10, typically, is of ogival form and converges to this bore. The handle defines a first recess 18 and a second recess 19 which extend through the side wall of the handle to its exterior surface from the cavity in a direction transversely of the handle. The recesses are substantially identical and are square, as viewed in such a direction. In a direction longitudinally of the handle, the recesses are disposed centrally between the ends of the handle and are aligned in such a direction, the first recess being spaced a predetermined distance toward the tip end from the second recess.

The instrument has an arm assembly 30 which is unitarily constructed of any suitable resilient material such as steel and has a first elongated arm 31; a second elongated arm 32 and a ring 33. The ring circumscribes the handle 10 adjacent to its base end 13 and is fixedly mounted on the handle. The arms are disposed transversely oppositely and exteriorly of the handle and extend longitudinally thereof with the first arm being aligned and overlaying the recesses 18 and 19. Each arm has a proximal end 35 directly connected to the ring, and the arm extends longitudinally of the handle from this end to a distal end 36 of the arm, this latter end being provided with a jaw 37. Each handle thus has a central portion 38 extended between its ends and alongside of the handle. It is evident that the proximal end is fixedly connected to the handle toward the base end thereof and that the exterior surface 11 of the handle is disposed toward the central portion of the first arm. The distal ends and the jaws are extended from the handle in a direction longitudinally thereof beyond its tip end and are thus spaced from this end in such direction, the jaws being aligned in a direction transversely of the handle.

The arms 31 and 32 are configured so that, when they are in an unconstrained configuration 40, their central portions 38 are each spaced somewhat from the handle 10 in a direction transversely thereof and the jaws 37 are spaced apart in such a direction. The central portion of each arm has a surface 42 disposed oppositely of the handle. It is evident that the arms are mounted on the handle so that grsping the arms individually at such surfaces urges the arms to bend toward the handle moving their respective jaws together until the arms attain a grasping configuration 45, shown in dash lines in FIG. 2, in which the jaws engage. It is also evident such bending of the arms strains them so that each is resiliently urged to return to their unconstrained configuration. The arms thus serve to urge the jaws apart. The arms are substantially identical except that the central portion of the first arm 31 bears a protuberance 47 extended from this portion toward the first recess 18 and terminating at a second surface 48 of this arm. The second surface is thus disposed toward the handle and is closely adjacent to the side wall 11 when the first arm is in the unconstrained configuration. The first recess thus opens toward the projection, and the projection is proportioned and dimensioned to enter therein as the first arm moves toward the grasping configuration.

The subject instrument has an elongated cylindrical rod 50 which is coaxially related to the handle 10 and is received in the cavity 15. The rod has a solid portion 51 disposed toward the tip end 12, this portion being constructed of hardened steel or the like and having an exterior diameter such that it is slidably fitted to the bore 17 of the cavity 15. The solid portion bears a pointed piercing end 52 of the rod. The piercing end is disposed at the tip end of the handle, and the solid portion extends from the tip end longitudinally and centrally within the cavity in a direction oppositely of the piercing end. The solid portion has, centrally, a pair of lugs 54 extended diametrically oppositely from it. The lugs are disposed on the rod so that the lugs are within the cavity and are spaced substantially from the tip end. The rod has an elongated and cylindrically tubular extension 56 which is closely fitted in coaxial relation to the rod. One end of the extension engages the lugs oppositely of the piercing end, and the extension continues from the lugs beyond the solid portion to an end 57 of the rod opposite its piercing end 52. It is evident that the rod extends longitudinally of the handle and within the cavity and that the rod is received therein and is slidably fitted to the handle at the bore 17 for movement in a direction longitudinally of the cavity. The rod is movable in such a direction between an extended or operating position 61, best shown in FIG. 1, and a retracted or sheathed position 62, best shown in FIG. 2. The rod moves between these positions a distance substantially equal to the predetermined distance between the recesses 18 and 19. In the operating position, the rod extends longitudinally of the handle from the cavity and the tip end and extends between the jaws 37 with the piercing end disposed beyond the jaws from the tip end. In the sheathed position, the piercing end is disposed adjacent to the tip end and is disposed from the jaws in a direction toward the base end 13 of the handle from its tip end.

The instrument has a compression spring 65 extended within the cavity 15 between the tip end 12 of the handle 10 and the lugs 54 of the rod 50. The spring is disposed in coaxial and circumscribing relation to the rod. It is evident that the spring is mounted on the handle and resiliently urges the rod to move longitudinally of the handle in a direction from the operating position 61 toward the sheathed position 62.

The instrument has a plunger 70 disposed at the base end 13 of the handle 10. The plunger has a cylindrical portion 72 which is slidably fitted to the cavity 15 at this end, the plunger being received in the cavity for movement longitudinally thereof. The plunger extends longitudinally of the handle in opposite direction from the base end. The plunger thus has a manually actuatable button 73, which is spaced outwardly of the handle, and has a surface 74, which is disposed within the cavity toward the end 57 of the rod 50. This end of the rod is held in engagement with such surface by the spring 65. It is evident that the rod carries the plunger in a direction from the tip end 12 toward the base end 13 as the rod moves from the operating position 61 toward the sheathed position 62. It is also evident that pressing the button toward the handle moves the plunger toward the tip end and carries the rod toward the operating position against the resilient urging of the spring, thereby serving to extend the piercing end 52 from the handle. The plunger includes a pair of arms 76 disposed within the cavity. The arms extend parallel to the extension 56 of the rod from surface 74 to the vicinity of the recesses 18 and 19. The arms are disposed diametrically oppositely of the rod in a plane normal to a plane intersecting the recesses 18 and 19. Each arm has a pair of protuberances disposed oppositely of the rod for engagement with the handle. The plunger is unitarily constructed of resilient plastic material and is configured so that the protuberances resiliently engage the handle for guidance of the plunger as it moves therein.

The instrument has a latch assembly 80 mounted on the plunger 70 for movement therewith longitudinally of the cavity 15. This assembly has an arm 81 extended parallel to the rod from the plunger surface 74 in a plane intersecting the first recess 18 and the second recess 19. The assembly, preferably, is of resilient plastic material and is unitarily constructed with the plunger. The arm is thus resilient and has one end directly connected to the plunger and has an opposite end. The opposite end bears a projection 82 which is of triangular configuration, as viewed normal to such plane, this projection being proportioned and dimensioned to enter either of the recesses. The arm is configured resiliently to urge the projection radially outwardly of the handle and the projection is disposed to enter the first recess when the rod is in the operating position 61 and to enter the second recess when the rod is in its sheathed position 62. It is evident that the projection is mounted on the plunger for movement independently thereof in a direction transversely of the handle. The projection has a first surface 84 which lies in a plane normal to the axis of the handle and is disposed toward the base end 13 of the handle. This surface extends from the arm a distance substantially equal to the radial thickness of the handle side wall to an apex 85 of the projection, and the projection has a second surface 86 extended from the apex toward the tip end 12 and angularly related to the first surface.

It is evident that, when the projection 82 is aligned with the first recess 18 or with the second recess 19, the projection is resiliently urged into such aligned recess by the arm 81 so that the projection is received in the recess. The first surface 84 of the latch assembly thus engages the recess in latching engagement therewith and latches the rod 50 to the handle 10 in the one of the positions 61 or 62 corresponding to the recess so engaged. The rod is thus retained in the operating position 61 when urged thereinto by the plunger 70, and it is evident that the first surface 84 and the projection define a latch mounted on the plunger to so retain the rod. As shown in FIG. 2, when the rod is in the operating position, the protuberance 47 of the first arm 31 is juxtapositioned to the second surface 86 of the projection. It is apparent that this second surface extends toward the surface 48 of the protuberance and is movable in a direction from such surface of protuberance toward the handle 10. As a result, bending the first arm from its unconstrained configuration 40 toward the handle and toward its grasping configuration when the rod is latched to the handle in its operating position, causes the protuberance 47 to engage the projection 82 at its second surface, as indicated by the numeral 88, and carries the projection into the cavity 15, unlatching the rod from the handle. The spring 65 then motivates the rod toward the sheathed position 62. It is apparent that the protuberance 47 is mounted on the handle together with the first arm and is operably connected to the central portion 38 of this arm for actuation of the latch assembly 80. It is also apparent that the projection 82 and its surface 86 define a trigger extended toward the protuberance 47 and movable in a direction from the protuberance toward the handle to unlatch the rod therefrom when the first arm is manually actuated toward the latch assembly and when the surface 74 is in latching engagement with the first recess 18.

As best seen from FIGS. 2 and 3, when the rod 50 is in the sheathed position 62, the projection 82 engages the second recess 19 and latches the rod in such position. If the projection is then manually engaged with any suitable object to depress the projection into the cavity 15, the plunger 70 and the rod are unlatched from the handle and are urged therefrom by the spring 65 into a partially disassembled configuration, indicated by the numeral 90, in which the plunger is not received in the cavity and the rod projects from the base end 13 of the handle.

Certain elements of the subject instrument utilized in latching the rod 50 in its operating position 61 and in its sheathed position 62 and for unlatching the rod from the recesses 18 and 19 for movement from these positions are very similar in structure and mode of operation to corresponding elements of a prior art mechanism used in a ball-point pen or the like having an elongated pen cartridge which is selectively extendable from or retractable within a handle. These elements of the subject instrument are the recesses 18 and 19, the spring 65, the plunger 70, and the latch assembly 80. In the prior art mechanism for use in a pen, a protuberance, which has an unlatching function corresponding to the unlatching function of the protuberance 47, is mounted on the distal end of a resilient clip for attaching the pen to a shirt pocket or the like.

OPERATION

The operation of the described embodiment of the subject invention is believed to be clearly apparent and is briefly described at this point. Normally, the instrument is stored or carried with the rod 50 in its sheathed position 62 to prevent damage to or by the piercing end 52. When it is desired to extract a splinter or the like from the flesh of a finger or other part of a body, the button 73 is pressed toward the handle 10 until the projection 82 enters the first recess 18 under the resilient urging of the arm 81, thereby latching the rod into its operating position 61 and configuring the instrument for piercing flesh around the splinter for access thereto. No other manipulation is required to so configure the instrument than to press the button. The splinter is then exposed with the piercing end, the instrument being grasped by the handle or by the first arm 31 and/or the second arm 32 without pressing the arm toward the handle.

It is evident that when the rod 50 is in its operating position 61, as shown in FIG. 1, the portion of the jaws 37 to one side of the piercing end 52 are available to grasp between the portions a fold of skin adjacent to a splinter embedded in the body. When the skin about the splinter is so grasped, the skin is stretched to facilitate exposure of the splinter by drawing the instrument away from the splinter while the piercing end is employed to pierce the skin and expose the splinter.

When the splinter is exposed, the surface 42 of the first arm 31 is pressed toward the handle 10 unlatching the rod 50 from the handle so that the rod automatically and, substantially instantly, assumes the sheathed position 62 as previously described. It is evident that the rod is returned to this position without substantially changing the grip as would be required, for example, if the instrument required its base end to be juxtapositioned to an exposed splinter. As soon as the rod assumes the sheathed position, it is evident that the jaws 37 are juxtapositioned to the exposed splinter to grasp the same by continuing to press the first arm toward the handle. It is evident that no manipulation of the instrument is required to bring the rod to its sheathed position other than the initial movement of the first arm required to bring the arms into their grasping configuration 45 onto the splinter.

If it is necessary to replace the solid portion 51 of the rod 50 because, for example, the piercing end 52 has been blunted, or if access is desired to this end for cleaning or sterilizing it, the instrument is brought into its disassembled configuration 90, as before described. The piercing end is then removed from the handle by grasping the portion of the extension 56 projected from the base end and drawing the rod from the cavity 15. The instrument, subsequently, is conveniently reassembled by inserting the rod into the cavity, the solid portion 51 being entered into the bore 17 with the piercing end 52 leading. The plunger 70 is then inserted into the cavity until the assembly 80 mounted on the plunger 70 latches the rod in the sheathed position.

Although the invention has been herein shown and described in what is conceived to be the most practical and preferred embodiment, it is recognized that departures may be made therefrom within the scope of the invention, which is not to be limited to the illustrative details disclosed.

Having described my invention, what I claim as new and desire to secure by Letters Patent is:

1. An instrument for extracting splinters and the like comprising:
  A. an elongated handle having a pair of opposite ends and defining a central cavity extended longitudinally within the handle from one such end;
  B. a pair of elongated arms which are mounted on the handle and disposed transversely oppositely and exteriorly thereof and are extended longitudinally thereof, the arms having respective jaws which are extended longitudinally from the handle beyond said one end and are aligned in a direction transversely thereof, one of the arms being mounted on the handle for movement of the jaw thereof from the other of the jaws and toward such other jaw for engagement therewith, and such one arm having means for resiliently urging the jaw thereof from such other jaw;
  C. an elongated member having a piercing end and an opposite end, said member extending within the cavity with the piercing end disposed at such one end of the handle and said member being received in the cavity for movement longitudinally of the cavity between a retracted position in which the piercing end is longitudinally spaced from the jaws in a direction toward the end of the handle opposite such one end and an extended position in which said end is extended beyond the jaws longitudinally of the handle from the cavity and said one end;
  D. retracting means for resiliently urging the elongated member longitudinally of the handle in a direction from the extended position toward the retracted position;
  E. manually actuatable extending means for urging the elongated member into the extended position from the retracted position against the urging of the retracting means;
  F. means for latching the elongated member to the handle to retain said member in the extended position when the elongated member is urged thereto by the extending means; and
  G. manually actuatable means for unlatching the elongated member from the handle when said member is latched thereto in the extended position so that said member moves to the retracted position under the urging of the retracting means.

2. The instrument of claim 1 wherein
  A. said one arm has a first surface disposed oppositely of the handle for manual engagement to move said arm toward the handle and move the jaw of said arm toward such other jaw and has a second surface disposed toward the handle, and
  B. the means for unlatching the elongated member from the handle comprises a trigger extended toward said second surface and movable in a direction from said surface toward the handle to unlatch the elongated member therefrom so that movement of said one arm toward the handle to engage the jaws when the elongated member is latched in the extended position unlatches said member from the handle for movement into the retracted position.

3. The instrument of claim 2 wherein:
  A. each of the arms is constructed of resilient material and has a proximal end fixedly connected to the handle toward the end thereof opposite said one end and a portion which extends alongside the handle from the proximal end to the corresponding jaw, said portion being configured so that, when the arm is in an unconstrained configuration, said portion is spaced transversely of the handle so that grasping the arms individually oppositely of the handle urges the arms to bend theretoward moving the jaws together and straining the arms so that the arms are resiliently urged to return the unconstrained configuration, and said one arm has a projection extending from said portion thereof toward the handle and bearing said second surface;
  B. the handle defines a recess therein opening toward the projection; and
  C. the trigger is received in the recess so that, when the one arm bends from said such configuration toward the handle, said projection engages the trigger to unlatch the elongated member from the handle.

4. An instrument for extracting splinters and the like comprising:
  A. an elongated handle having a pair of longitudinally opposite ends and defining a cavity which extends longitudinally through the handle and opening through such end, and a recess which extends from the cavity in a direction transversely of the handle;
  B. a pair of elongated arms constructed of resilient material, each arm having a distal end bearing a jaw which is spaced outwardly of one of the opposite ends of the handle in a direction longitudinally therealong and is aligned in a direction transversely of the handle with the jaw of the other arm; having a proximal portion fixedly connected to the handle toward the opposite end thereof; and having a central portion extended between the distal end and the proximal end exteriorly of the handle, the arms being mounted on the handle transversely oppositely thereof and being configured so that, when the arms are unconstrained, each central portion is spaced from the handle in a direction transversely thereof and the jaws are spaced apart in such a direction;
  C. an elongated member disposed in the cavity and extended longitudinally of the handle, said member having a piercing end disposed at said one end of the handle and an opposite end and being slidably fitted to the handle for movement longitudinally thereof between a sheathed position in which the piercing end is disposed adjacent to said one end of the handle and an operating position in which the member extends from the cavity and from said one end between the jaws with the piercing end disposed oppositely of the jaws from said one end;

D. a plunger disposed in the cavity toward said opposite end of the handle and slidably received therein for movement longitudinally thereof, the plunger having a button spaced longitudinally thereof, the plunger having a button spaced longitudinally outwardly of the handle and being engaged with said opposite end of the elongated member;

E. retracting means mounted on the handle and engaged with the elongated member for resiliently urging said member to move toward the retracted position, so that said opposite end of the member engages the plunger and carries the plunger in a direction from the one end of the handle toward said opposite end thereof as the elongated member moves toward the sheathed position and so that pressing said button toward the handle moves the plunger toward said one end of the handle carrying the elongated member toward the operating position against the resilient urging of the retracting means;

F. a latch assembly mounted on the plunger for movement therewith longitudinally of the cavity, said assembly having a latch which is mounted on the plunger for movement independently of the plunger in a direction transversely of the handle and is disposed to enter the recess when the elongated member is in its operating position, and having means for urging the latch into latching engagement with the recess; and G. unlatching means mounted on the handle and operably connected to the central portion of one of the arms for actuating the latch assembly, when the one arm moves from its unconstrained configuration toward the handle, to urge the latch from the recess so that the retracting means motivates the elongated member toward the sheathed position.

5. The instrument of claim 4 wherein

A. the handle has an exterior surface disposed toward the central portion of said one of the arms and the recess extends transversely through the handle between said surface and the cavity, and B. the unlatching means comprises a projection mounted on said central portion and extended toward the recess for engagement of the latch assembly therein when said assembly is in said latching engagement.

* * * * *